United States Patent [19]

Goulter

[11] Patent Number: 5,380,312
[45] Date of Patent: Jan. 10, 1995

[54] ONE-PIECE MALE URINARY INCONTINENCE CONDOM, WITH A SKIN SHIELD, NON-RETURN VALVE, URINE COLLECTING COMPARTMENT, AND DRAIN VALVE

[76] Inventor: Victor H. Goulter, 485 Molimo Dr., San Francisco, Calif. 94127

[21] Appl. No.: 20,583

[22] Filed: Feb. 23, 1993

[51] Int. Cl.⁶ .............................................. A61F 5/44
[52] U.S. Cl. ................................................... 604/352
[58] Field of Search .............................. 604/349-352; 4/144.1-144.4; 128/760, 761

[56] References Cited

U.S. PATENT DOCUMENTS

| | | | |
|---|---|---|---|
| 3,835,857 | 9/1974 | Rogers, III et al. | 604/349 |
| 4,054,142 | 10/1977 | Tettes | 604/352 |
| 4,540,409 | 9/1985 | Nystrom | 604/349 |
| 4,971,074 | 11/1990 | Hrubetz | 604/349 |
| 5,009,649 | 4/1991 | Goulter et al. | 604/351 |

Primary Examiner—Randall L. Green
Assistant Examiner—Rob Clarke

[57] ABSTRACT

Device for use by males with incontinence problems, has an elastomeric urine collecting compartment sized to hold a quantity of urine which can be emptied when desired by removing a screw-off cap or pull-out plug at a men's urinal. Collecting compartment (23) is isolated from the penis by a skin shield (25) which incorporates a non-return valve (50) which allows urine to pass unrestricted into the collecting compartment, but prevents voided urine returning back to the penis inside the skin shield. An elastomeric tubular portion (37) is sized to fit snugly onto the penis shaft to prevent leakage and to retain its position in place on the penis. If necessary, the pressure of the tubular portion against the penis shaft can be increased by using an additional elastic 'hook and loop' VELCRO™ band (69). When fitting the catheter, it's open end (21) can be stretched over an applicator ring (61) making open end (21) and tubular portion (37) open enough for the user to slip the catheter in place over and onto the penis, after which the catheter is disengaged from the applicator ring. The ring is then removed entirely from the catheter, leaving the catheter securely in place.

10 Claims, 3 Drawing Sheets

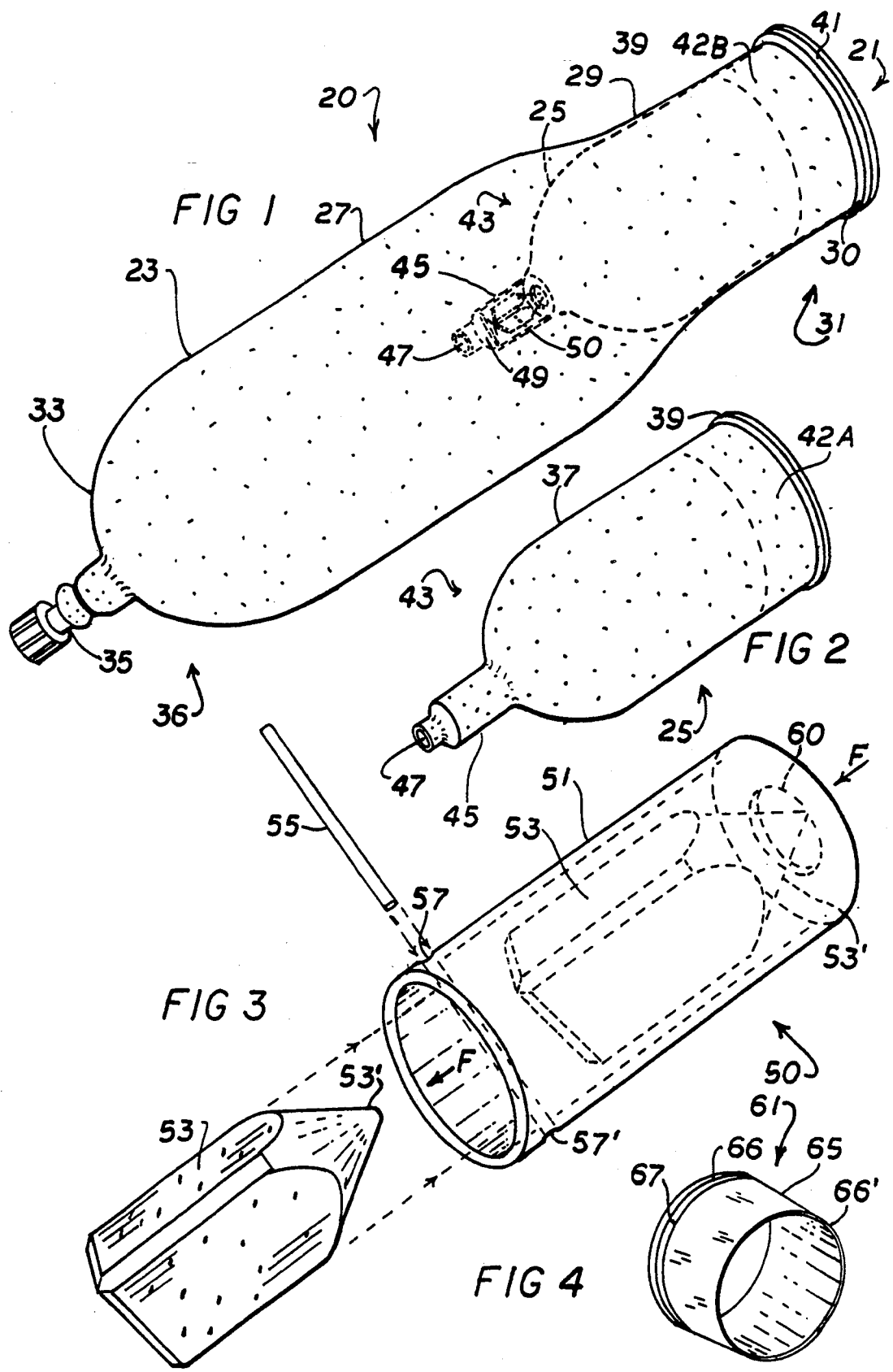

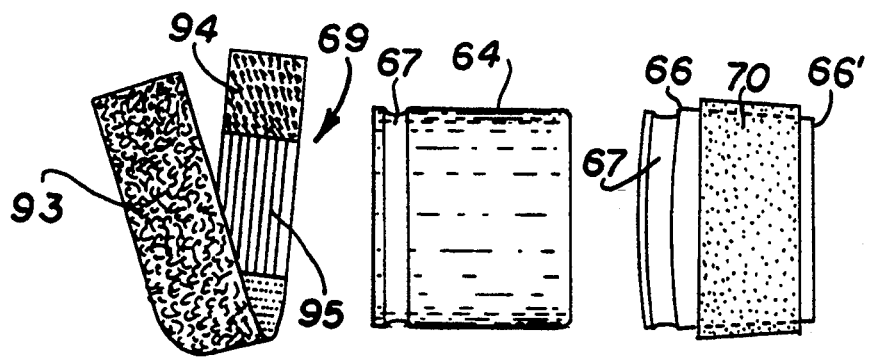
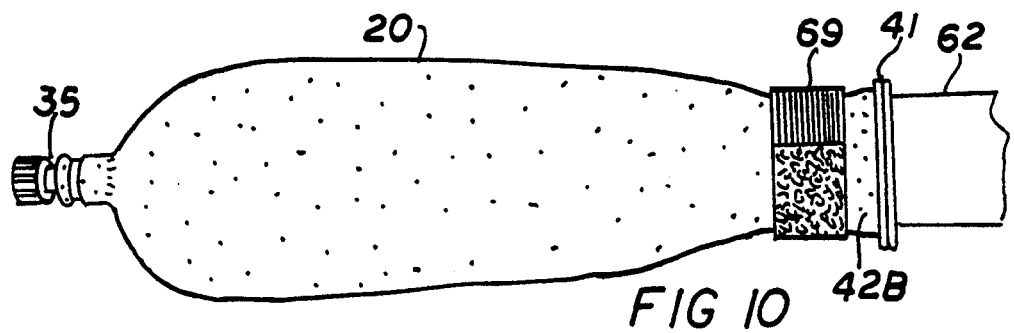
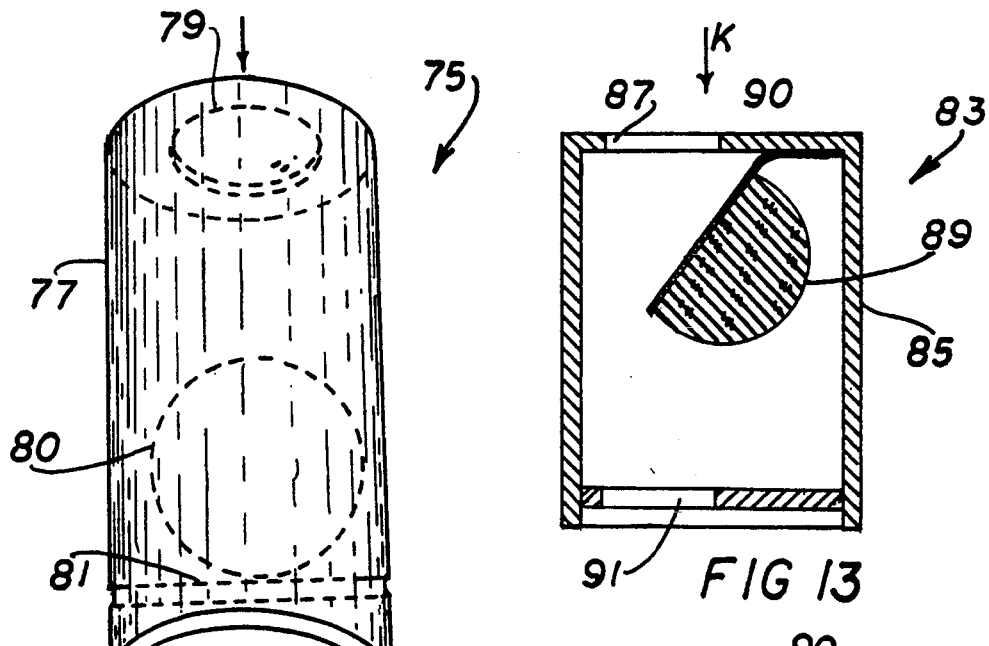
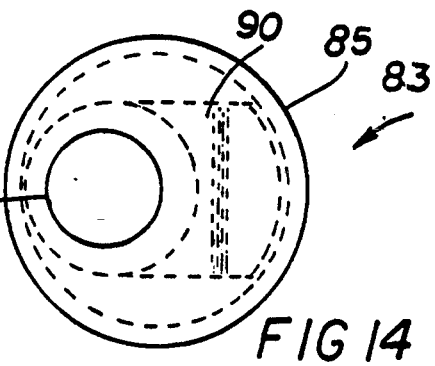

ONE-PIECE MALE URINARY INCONTINENCE CONDOM, WITH A SKIN SHIELD, NON-RETURN VALVE, URINE COLLECTING COMPARTMENT, AND DRAIN VALVE

BACKGROUND—FIELD OF INVENTION

The present invention is related to male urinary incontinence devices, in particular to a penile skin shield and a non-return valve.

BACKGROUND—DESCRIPTION OF PRIOR ART

U.S. Pat. No. 5,009,649, dated Jul. 13, 1989, issued to Victor Goulter and Barbara Goulter is incorporated by reference as part of the specifications of this invention for details of construction for similar components. In said patent, we described a urinary incontinence device which could be worn with comfort and which permitted the wearer to engage in most normal social and business activities, and provided many other advantages.

However, there were several disadvantages. One problem was that, in the event the device slipped off, heavy spillage was likely. Another disadvantage was that the penis was exposed to contact with the urine as it collected in the device, causing the possibility of skin irritation for those who needed to wear such a device around the clock. Another disadvantage was that, in the case of patients with AIDS or other communicable diseases, caretakers handling or removing the device or taking care of spills ran the risk of coming in contact with the patient's urine.

Another disadvantage was that a waterproof seal was required to prevent leakage, requiring the application of a smear of dental or a similar skin-compatible adhesive to hold the device in place, thus complicating the process of putting it on. Removal was also complicated by the need to thoroughly wash and soap the penis, to remove the adhesive after having removed the device.

In another condom-like incontinence device, U.S. Pat. No. 3,876,771, the complexities associated with putting the device on created many disadvantages. The user had to shave or trim the pubic area, then cut an opening in the "skin barrier," making it perfectly round and slightly larger than the width of the penis, in order to make the device fit. If too much was cut away, the device became useless; if too little, more had to be cut. According to the inventor's instructions, the user then had to lie in a supine position, while either he or a caretaker massaged the abdomen and drew the penis out of the body and manipulated the device into place, pressing the skin barrier up against the pubic area. Any wrinkling of the skin barrier during this process would result in leaks during wearing. Next, adhesive strips had to be used to band the device directly to the skin of the pubic area, and pressed in place for a full minute while the adhesive set. These complicated instructions made it virtually impossible for almost any user to put on the device without assistance, and difficult even with help.

Another set of disadvantages was associated with removal. It was recommended by the inventor that the user lie on his back while a water-based Jelly was applied to soften the adhesive, after which the adhesive strips and device were lifted from the skin in the direction of hair growth. Not only was such a process likely to cause discomfort, but its complexity made it too difficult for most to manage without assistance.

Other disadvantages were associated with the usefulness of the device itself. The collection pouch was of rigid, inflexible, and non-expansive material, incapable of conforming its contours to the shape or holding capacity of men's undergarments, whether standard or modified, or of adapting its own holding capacity to the wearer's need. These problems added to the conspicuous of the device while being worn and also the likelihood of overflows and spills. Due to the stiffness and inflexibility of the device, the wearer would suffer discomfort and also have difficulty getting it out from his clothes in order to drain it. Also, due to poor design, the tip of the penis was continually bathed in urine.

OBJECT AND ADVANTAGES

Accordingly, one object and advantage of the present invention is to provide a condom-like male urinary incontinence device which is spill-proof and leak-proof. A further object is to entirely protect the skin of the penis from contact with the urine collected in the condom, preventing skin irritation, and making the device practicable for use around the clock. Another is to provide a device which can be used without assistance by all but the severely handicapped.

Another object and advantage is to provide a device which requires no adhesive to stay in place. Another object is provide a quick and easy method of putting the device on. Yet another object and advantage is to provide a device for simple, painless removal.

Still further objects and advantages are to provide a device which readily conforms to the shape and capacity of a modified men's undergarment, and to provide a device which is inconspicuous and can easily be emptied in a men's public urinal or similar setting without causing embarrassment to the user.

Additional objects and advantages are to provide a device which is inconspicuous when worn under normal street clothes, and also one which can be used by astronauts, fighter pilots, police on special duty, and other men who cannot leave their station to visit a restroom. Another object is to provide a device which does not require an extensive program of training in its use.

BRIEF DESCRIPTION OF DRAWINGS

FIG. 1 is a perspective view of a condom catheter of the present invention together with an integral skin shield, or inner condom sheath.

FIG. 2 is a perspective view of the integral skin shield or condom sheath portion of the condom catheter of FIG. 1.

FIG. 3 is an enlarged perspective view of a non-return valve used in the skin shield.

FIG. 4 is a perspective view of an applicator used on the condom to simplify attaching the condom to the wearer.

FIG. 9 is a perspective view of an elastic hook and loop band used with the condom.

FIG. 10 is a perspective view of an elastic hook and loop band attached to a condom on a wearer.

FIG. 11A is a perspective view of a second embodiment latex band fitted around the applicator 'for attaching to a condom on a wearer.

FIG 11B is a side perspective view of an applicator having parallel sides.

FIG. 12 is a second embodiment non-return valve for use with the skin shield.

FIG. 13 is a sectioned view of a third embodiment non-return valve used with the skin shield.

FIG. 14 is a top view of the third embodiment taken in the direction of arrow "K" of FIG. 13.

DETAILED DESCRIPTION—FIGS 1-3

Figure 5:
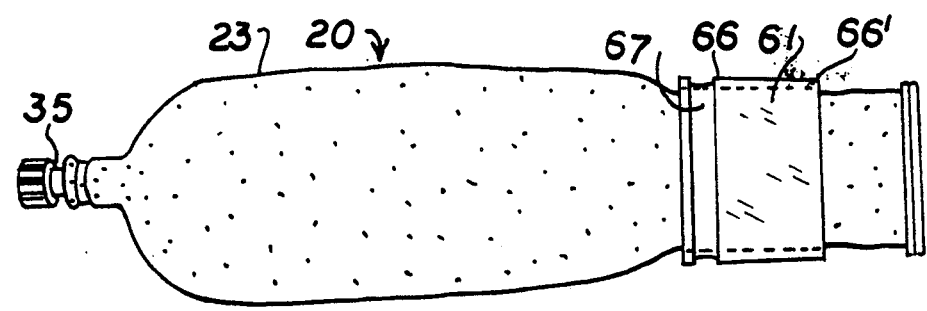
FIG. 5 is a side perspective view of the applicator of FIG. 4, showing the first stage of attaching it to the condom.

FIG. 1 shows a male urinary condom catheter device 20 according to the invention. It is made of an elastomeric material such as rubber latex, having such desirable elastic properties as softness, water-resistence, puncture-resistence, and conformity to both the wearer's body and his clothing. It has a large open end 21 which divides into two compartments, i.e., an outer-urine collecting compartment 23, and a skin shield, or inner condom sheath, 25.

Outer Urine-Collecting Compartment—FIG 1

Urine-collecting compartment 23 is made of an elastomeric material such as rubber latex and is sized to comfortably hold about 8 to 16 fluid ounces of urine, unstretched, and capable of stretching to contain larger amounts as urine accumulates. Although urine-collecting compartment 23 is capable of expanding to hold a gallon or more without bursting, it is unlikely that a user will tolerate so much weight and bulk before emptying the compartment.

Urine-collecting compartment 23 comprises an enlarged central portion 27, an open end cylindrical portion 29, and a thickened rim 30 at its proximal end 31. It has a closed end 33 and a "screw-off" or pull-out "plug valve" fluid outlet 35 at its distal end 36.

It is a design feature of the invention to provide a urine collecting compartment 23 of sufficient capacity, such that the bulk of the accumulated urine will become noticeable to the user and remind him of the need to empty it before expansion under pressure takes place within compartment 23, resulting in urine being forced back against non-return valve 53.

Integral Skin Shield or Condom Sheath—FIGS 1-3

Skin shield 25 comprises a tubular portion 37 which has a thickened rim 39 and is imperviously sealed to a similar thickened rim 30 of condom 20 to form a finger-grippable end enlargement rim 41 (FIG. 1). A half inch wide section 42A of tubular portion 37 of skin shield 25 is also imperviously sealed to a similar section 42B of cylindrical portion 29 of condom 20 at its proximal end 31. The distal end 43 of skin shield 25 is reduced in diameter to form a nipple 45 with a fluid passage 47 and a cavity 49 (FIG. 1). Housed within cavity 49 of nipple 45 is a non-return valve 50.

Non-return Valve—FIGS 1-3

As the term implies, non-return valve 50 (FIGS. 1 and 3) permits fluid to flow unrestricted in one direction through it, in the direction of arrow "F", but prevents fluid flowing in the opposite direction. It is frictionally fitted within cavity 49 of nipple 45 (FIG. 1) and retained in place by the elastic pressure of nipple 45.

Non-return valve 50 comprises a hollow barrel portion 51 (FIG. 3), a pointed floating cork valve 53, and a retaining pin 55. Retaining pin 55 is inserted through barrel portion 51 in holes 57 and 57', thereby capturing cork valve 53 within a free-floating environment inside hollow barrel portion 51. Cork valve 53 is triangular in cross section and is loose-fitting within the walls of hollow barrel portion 51, such that when voided urine enters through open valve seat 60, under the influence of gravity, it will flow unrestricted past float valve 53, through fluid passage 47, and into urine collecting compartment 23.

As voided urine continues to collect in compartment 23 it level will rise within the proximity of non-return valve 50. At times, due to physical movement of the wearer, urine will re-enter through fluid passage 47 and come into contact with float valve 53, which, due to its capacity to float on liquid, will rise upward until pointed end 53' engages valve seat 60, thereby closing off entry of urine into skin shield 25. By this means, accumulated urine is prevented from making contact with the skin of the penis housed within skin shield 25.

In many positions of the body, non-return valve 50 will not be vertically oriented, but will be positioned at an inclined angle. Nevertheless, as the liquid level rises, float valve 53 will be urged by its floating capacity toward seat 60, engaging the valve seat and preventing urine entering skin shield 25.

Applicator Ring—FIGS 4-8 11A and 11B

FIG. 4 shows a cone-shaped condom applicator ring 61, made from plastic, or any other suitable material. Its inside diameter is greater than the diameter of penis 62 (FIG. 7) or cylindrical portion 29 of condom 20 (FIG. 1). Ring 61 can be tapered as in FIG. 4 and 11A or have parallel sides 64 (FIG. 11B)

Tapered applicator ring outer surface 65, provides a sloping surface which makes for easier removal of folded portion 63 of condom 20 than is the case with parallel-sided applicator 64 (FIG. 11B). However, applicator 64 is significantly less expensive to manufacture. On both models, a finger-grip annular groove 67 is provided for ease of holding.

Method of Using Applicator—FIGS. 4-10

Figure 6:
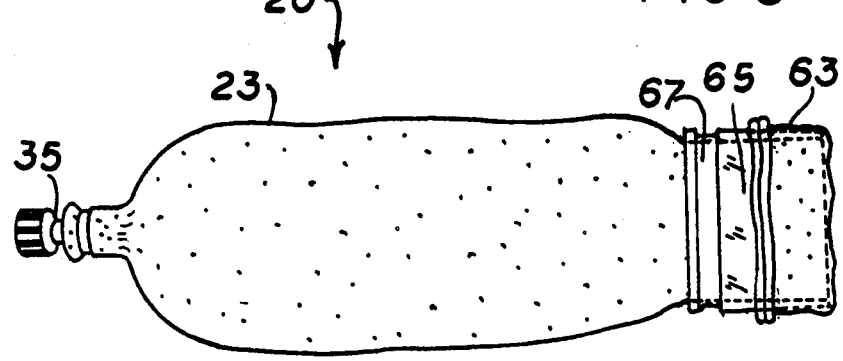
FIG. 6 is a side perspective view of the applicator of FIG. 4, showing the second stage of attaching it to a condom.

In use, end 21 of condom 23 is first fitted through applicator ring 61 from thick end 66 toward the thin end 66' (FIG. 5). A short length 63 of the open end 21 is then stretched over and folded back around outside 65 of applicator 61 (FIG. 6).

Figure 7:
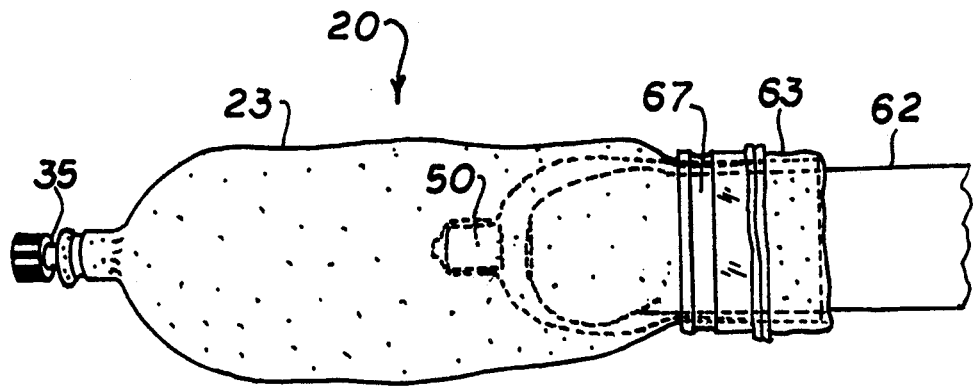
FIG. 7 is a side perspective view of the applicator used to fit the condom in place on the user.

Open end 21, together with applicator 61 is then placed over and down along penis 62 until the head of the penis is near non-return valve 50 (FIG. 7)

Figure 8:
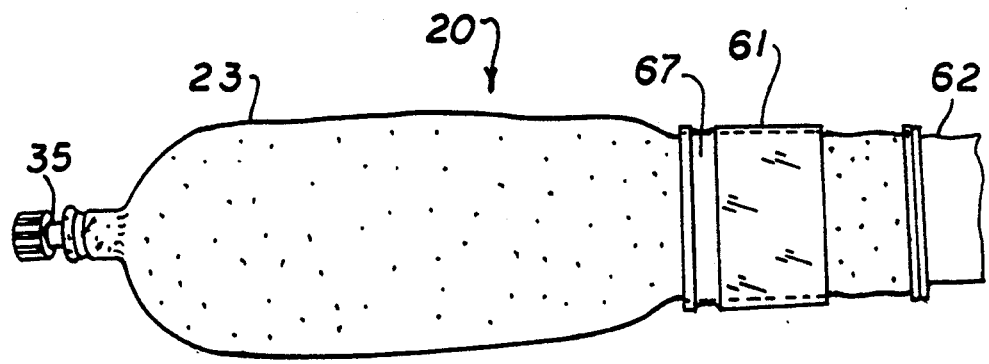
FIG. 8 is a side perspective view of the condom released from the applicator.

Folded portion 63 is then unfolded off thin end 66' of applicator ring 61 so that it is around the shaft of penis 62, as shown in FIG. 8. While holding the condom in position with one hand the applicator can then be slipped over and off the condom with the other hand.

A hook and loop/elastic (VELCRO) band 69 (FIG. 9) can then be fitted with just enough tension around the unfolded portion 63 of condom 20, to prevent it from coming off (FIG. 10). The degree of tension required can be learned by trial-and-error. Typically, a 7-13 mm (0.3"-0.5") stretch of the elastic portion of band 69, before engaging hooks to loops, provides sufficient tension to hold condom 20 on the penis.

Hook and Loop/Elastic Band—FIG. 9

FIG. 9 shows a hook and loop/elastic band 69, comprising three parts; a 70-80 mm (2.75"-3.25") length of loop band X 19 mm (0.75") wide, a 60-70 mm (2.375"-2.75") length of elastic band X 19 mm (0.75") wide, and a 15 mm (0.625") length of hook band X 19 mm (0.75") wide. Loop band 93, and hook band 94 are sewn on opposite ends of elastic band 95, each with an overlapping length portion of about 13 mm (½"). The total length of the hook and loop/elastic band is about 140 mm (5.5") long. It can stretch to about 155 mm, (6.5") in length.

Second Embodiment Latex Band

Alternatively, a latex band or ring 70 can be used in place of hook and loop/elastic band. It is first stretched around the applicator, as shown in FIG. 11, then applicator with latex band is slipped over the condom and penis and into position over the proximal end of the condom covering the penile shaft. The band is then pushed off thin end 66' of applicator 61 onto the condom, to hold and secure it to the penis.

The band comprises a ring of latex about 25 mm (1") inside diameter, X 19 mm (0.75") wide X 1 mm (0.039") wall thickness.

Although not adjustable as is the hook and loop/elastic band, latex bands are significantly less expensive to manufacture and can readily be made in a variety of sizes.

Second and Third Embodiments, Non-Return Valves—FIGS. 12-14

A second embodiment non-return valve 75 is shown in FIG. 12, which comprises a cylinder 77 with an end valve seat 79, a floating ball valve 80, and a retaining bar 81.

A third embodiment non-return hinged floating valve 83 is shown in FIG. 13 and 14, which comprises a housing 85, with a circular valve seat 87, a cork float 89, attached to a flexible hinge strap 90, and a water outlet hole 91.

Both ball valve and floating valve embodiments operate in like manner to floating cork valve shown in FIG. 3. Their manufacturing costs are not envisioned to be significantly different.

All non-return valves react to prevent liquids from passing back in the direction from which they came. Many, however, require more fluid pressure to open the valve than is provided by the flow of urine from the penis. Such valves would not be suitable for this device, as some urine would remain behind, trapped within the inner condom sheath, along with the penis. The non-return valves of FIGS. 3, 12, 13, and 14 have in common the capacity to allow a liquid, such as urine, an unrestricted and complete one-way fluid passage, so that the inner condom sheath is thoroughly drained and the penis is never immersed in urine.

Summary, Ramification, and Scope

Thus, the reader will see that I have provided a male incontinence device which is far superior to any prior art device, due to having both an integral skin shield or sheath and a non-return valve which isolates the penis from voided urine. In addition I have provided a device which can give comfort and protection from infection caused by unsuitable alternative devices, a device which also allows voided urine to enter a collecting compartment without any restriction, yet immediately forms a non-return barrier between the urine collecting compartment and the penis within the skin shield or sheath.

Furthermore, I have provided a device which requires no skin-compatible adhesives to hold it from slipping off, and no prolonged clean-up activity after it is removed. I have provided a device which can be comfortably emptied in a men's public urinal, without embarrassment to the wearer. In addition I have provided a device which is soft to the touch, comfortable to wear, and which readily conforms to the space and shape of men's undergarments and particularly to modified undergarments. It is also a device which is inconspicuous when used with normal street clothes, as well as being quick and easy to put on and take off. It is spill-proof and leak-proof and is safer for nurses attending to patients with AIDS or other infectious diseases. It can be used round the clock and worn in bed, and can, if preferred, be connected to a tube leading to an alternative storage container. It can be worn by fighter pilots and other who cannot leave their stations to visit a urinal. It can be used without assistance by all but the severely handicapped. It does not require a long teaching program to master its use, and it can be manufactured at a price affordable to virtually anyone in need of it.

While the above description contains many specificities, the reader should not construe these as limitations on the scope of the invention, but merely as exemplifications of preferred embodiments thereof. Those skilled in the art will envision that many other possible variations are within its scope. for example, skilled artisans will readily be able to change the dimensions and shapes of the various embodiments, such as by making the device from other materials, fitting other alternative valves and non-return valves or devices, or even providing some form of garment to assist in holding it on the wearer, or straps to replace the hook and loop/elastic band.

Accordingly, the reader is requested to determine the scope of the invention by the appended claims and their legal equivalents, and not by the examples which have been given.

I claim:

1. (amended) A male incontinence device, comprising:
    a first compartment sized to fit over the penis of a wearer,
    a second, urine-collecting compartment defined by a condom having a closed distal end and an open proximal end and being sized so that it can be fitted over at least the distal end of the penis of a wearer and further wherein at least the distal end of the condom is extensible when partially filled with urine,
    a skin shield which separates the interior of the first compartment and the interior of the second compartment,
    a fluid passage connecting said first compartment to said second compartment,
    and securing means for securing at least a portion of the first and second compartments to the penis of the wearer.

2. The male incontinence device of claim 1 further comprising a non-return valve within said fluid passage which allows fluid to flow from said first compartment to said second compartment and which prevents fluid from flowing from said second compartment to said first compartment.

3. The male incontinence device of claim 1 further comprising a float valve within said fluid passage which allows fluid to flow from said first compartment to said second compartment and which occludes said fluid passage to prevent fluid from flowing from said second compartment to said first compartment when said second compartment is full of fluid.

4. The male incontinence device of claim 1 further comprising a fluid outlet connected to said second compartment for draining fluid from said second compartment.

5. The male incontinence device of claim 1 wherein said first compartment is made of an elastomeric material which conforms to the penis of the wearer.

6. The male incontinence device of claim 1 wherein said securing means is an elastomeric band.

7. The male incontinence device of claim 6 wherein said elastomeric band has a first end and a second end which have coacting members of a hook and loop fastener attached thereto, whereby said elastomeric band can be wrapped around said first compartment where it fits over said penis and secured with said hook and loop fastener.

8. The male incontinence device of claim 1 further comprising a ring which has an inside diameter which is greater than the diameter of said penis, said ring being positionable within said proximal end of said first compartment to facilitate placement of said first compartment around said penis.

9. The device of claim 1, wherein said urine-collecting compartment has a volume of at least 8 ounces.

10. The device of claim 1, wherein said urine-collecting compartment is distensible for a greater volume of at least 16 ounces.

* * * * *